United States Patent
McKay et al.

(10) Patent No.: US 12,018,970 B2
(45) Date of Patent: Jun. 25, 2024

(54) WELL BORE FLUID SENSOR, SYSTEM, AND METHOD

(71) Applicant: Expro North Sea Limited, Dyce (GB)

(72) Inventors: John Henry McKay, Stonehaven (GB); David Sirda Shanks, Newmachar (GB)

(73) Assignee: EXPRO NORTH SEA LIMITED, Dyce (GB)

(*) Notice: Subject to any disclaimer, the term of this patent is extended or adjusted under 35 U.S.C. 154(b) by 159 days.

(21) Appl. No.: 17/733,179

(22) Filed: Apr. 29, 2022

(65) Prior Publication Data
US 2022/0349740 A1 Nov. 3, 2022

(30) Foreign Application Priority Data
Apr. 30, 2021 (GB) ..................................... 2106225

(51) Int. Cl.
| | | |
|---|---|---|
| *E21B 47/047* | (2012.01) | |
| *E21B 47/00* | (2012.01) | |
| *E21B 47/01* | (2012.01) | |
| *E21B 47/113* | (2012.01) | |
| *G01F 23/263* | (2022.01) | |
| *G01N 27/08* | (2006.01) | |

(52) U.S. Cl.
CPC ............ *G01F 23/268* (2013.01); *E21B 47/00* (2013.01); *E21B 47/01* (2013.01); *E21B 47/047* (2020.05); *E21B 47/113* (2020.05); *G01N 27/08* (2013.01)

(58) Field of Classification Search
CPC ...... E21B 47/00; E21B 47/113; E21B 47/047; E21B 47/10; G01N 27/08
See application file for complete search history.

(56) References Cited

U.S. PATENT DOCUMENTS 3,279,249 A * 10/1966 Tocanne ............... G01N 27/226
 73/19.09
5,929,342 A  7/1999 Thompson
(Continued)

FOREIGN PATENT DOCUMENTS

GB  2227841 A * 8/1990  ........... E21B 47/102
GB  2386691 B  12/2003
(Continued)

OTHER PUBLICATIONS

EP search report for EP22169411.0 dated Sep. 2, 2022.
GB search report for GB2106225.2 dated Nov. 19, 2021.

*Primary Examiner* — Robert E Fuller
(74) *Attorney, Agent, or Firm* — Getz Balich LLC (57) ABSTRACT

A well bore fluid sensor is provided that includes an inner plate, a plurality of outer plates, first and second cable fixtures, and an electronics module. The inner plate defines a sensor interior cavity. The outer plates include a first outer plate and a second outer plate. The electronics module includes a resonant circuit and a power supply and is in signal communication with the inner plate and at least one of the first and second cable fixtures. The inner plate, the first and second outer plates, and the first and second cable fixtures are coupled together to form a unitary structure. The inner plate is electrically insulated from the first and second outer plates, the first and second cable fixtures. The first and second outer plates are electrically insulated from one another. The inner plate is capacitively coupled to the first and second outer plates.

20 Claims, 5 Drawing Sheets

(56) References Cited

U.S. PATENT DOCUMENTS

| | | | |
|---|---|---|---|
| 9,116,105 B2 * | 8/2015 | Veneruso | G01N 33/2823 |
| 2008/0253230 A1 | 10/2008 | Thompson | |
| 2015/0275661 A1 * | 10/2015 | Donzier | G01N 27/02 |
| | | | 73/152.55 |
| 2020/0386099 A1 * | 12/2020 | Siu | G01N 27/226 |

FOREIGN PATENT DOCUMENTS

| | | |
|---|---|---|
| GB | 2364777 B | 10/2004 |
| SU | 1051247 | 10/1983 |
| WO | 2015118332 A1 | 8/2015 |

\* cited by examiner

WELL BORE FLUID SENSOR, SYSTEM, AND METHOD

This application claims priority to GB Patent Appln. No. 2106225.2 filed Apr. 30, 2021, which is hereby incorporated herein by reference in its entirety.

BACKGROUND OF THE INVENTION

1. Technical Field

The present disclosure relates to a well bore instrument system and measurement sensors relating thereto in general, and to a sensing module for detecting types of fluid in particular.

2. Background Information

In the oil and gas industry, well bores are often monitored to determine characteristics of the well fluid present within the well bore such as the type(s) of fluid. A person of ordinary skill in the art will recognize that the type of fluid present (e.g., gas, water, saltwater, oil, etc.) can vary over time and/or at different depth positions within the well bore. Many existing fluid monitoring systems utilize an electronic sensor module disposed within the well bore; e.g., attached to a cable that extends into the well bore. An example of such a sensor is a capacitance sensor that has two plates in contact with the well fluid. The presence of saltwater in the well fluid can be a problem for such capacitance type sensors. Other sensors utilize relatively complex impedance circuits configured to simultaneously measure both conductive and dielectric properties of the well fluid. Many of these type sensors have an overall size that can create installation and deployment problems in the confined space of a well bore. PCT Publication No. WO 2015/019081 and United Kingdom Patent Publication No. GB 2386691A are examples of fluid monitoring systems that include sensors that may be used within a well bore.

Well bore environments are often harsh, with deeper regions having elevated pressures and temperatures as compared to regions nearer the surface. Sensors intended to be deployed at deep well bore positions must be designed with physical characteristics that enable the sensor to withstand elevated pressures and temperatures. These robust physical characteristics often make these sensors quite expensive to produce. In addition, traditional sensors capable of measuring fluid characteristics within the well bore tend to have a complex configuration. The complex configuration not only detrimentally adds to the cost, but often limits the useful life of these sensors.

What is needed is a sensor that can deployed in down hole environments, one that can withstand the elevated pressures and temperatures associated with such a downhole environment, one that has an extended useful life relative to existing sensors, and one that can be cost effectively produced.

SUMMARY

According to an aspect of the present disclosure, a well bore fluid sensor is provided that includes an inner plate, a plurality of outer plates, a first cable fixture, a second cable fixture, and an electronics module. The inner plate defines an axially extending interior cavity of the sensor. The plurality of outer plates includes a first outer plate and a second outer plate, both disposed radially outside of the inner plate. The first cable fixture is disposed at a first axial end of the sensor and the second cable fixture is disposed at a second axial end of the sensor. The electronics module includes a resonant circuit and a power supply, and the electronics module is in signal communication with the inner plate and at least one of the first cable fixture and the second cable fixture. The inner plate, the first outer plate, the second outer plate, the first cable fixture, and the second cable fixture are coupled together to form a unitary structure. The inner plate is electrically insulated from the first outer plate, the second outer plate, the first cable fixture, and the second cable fixture, and the first outer plate and the second outer plate are electrically insulated from one another, and the inner plate is capacitively coupled to the first outer plate and the second outer plate.

In any of the aspects or embodiments described above and herein, the sensor may be cylindrically configured. The inner plate has an inner diameter surface and an outer diameter surface, and the inner diameter surface defines the interior cavity.

In any of the aspects or embodiments described above and herein, the first cable fixture may be configured for attachment to a first cable portion, and the second cable fixture may be configured for attachment to a second cable portion in a manner that the sensor is disposed in-line between the first cable portion and the second cable portion.

In any of the aspects or embodiments described above and herein, the sensor may further include a first seal in communication with the first cable fixture, the first seal configured to provide a fluid seal to prevent fluid entry into the interior cavity of the sensor, and a second seal in communication with the second cable fixture, the second seal configured to provide a fluid seal to prevent fluid entry into the interior cavity of the sensor.

In any of the aspects or embodiments described above and herein, the sensor may include an electrical insulator disposed between the inner plate and the first outer plate and the second outer plate.

In any of the aspects or embodiments described above and herein, the sensor may be cylindrically configured. The inner plate may have an inner diameter surface and an outer diameter surface, and the inner diameter surface defines the interior cavity. The electrical insulator may be attached to a first portion of inner plate outer diameter surface disposed radially between the inner plate and the first outer plate and attached to a second portion of inner plate outer diameter surface disposed radially between the inner plate and the second outer plate.

In any of the aspects or embodiments described above and herein, the electrical insulator may include an inner diameter surface and an outer diameter surface, and the inner plate may be attached to the inner diameter surface of the electrical insulator.

In any of the aspects or embodiments described above and herein, the sensor may include a first electrical insulator ring disposed between the first cable fixture and the first outer plate, and a second electrical insulator ring disposed between the second outer plate and the second cable fixture.

In any of the aspects or embodiments described above and herein, the sensor may include a third electrical insulator ring disposed between the first outer plate and the second outer plate.

In any of the aspects or embodiments described above and herein, the electronics module may include a processor in communication with the resonant circuit and the power supply, the processor configured to receive signals from the resonant circuit and to control the power supply.

In any of the aspects or embodiments described above and herein, the sensor may be operable to sense a type of fluid within a well fluid based on a capacitance of the well fluid when in contact with the first outer plate or the second outer plate of the sensor, or both.

In any of the aspects or embodiments described above and herein, the sensor may be operable to sense a type of fluid within a well fluid based on a capacitance of the well fluid when in contact with the plurality of outer plates.

In any of the aspects or embodiments described above and herein, the sensor may be operable to determine a presence of water within a well fluid based on an electrical resistance of the well fluid when in contact with the first outer plate or the second outer plate of the sensor, or both.

According to another aspect of the present disclosure, a well bore fluid sensor system operable to sense well fluid within a well bore is provided. The system includes at least one sensor and an axially extending cable. The at least one sensor has an inner plate, a plurality of outer plates, a first cable fixture, a second cable fixture, and an electronics module. The inner plate defines an axially extending interior cavity of the sensor. The plurality of outer plates includes a first outer plate and a second outer plate, both disposed radially outside of the inner plate. The first cable fixture is disposed at a first axial end of the sensor and the second cable fixture is disposed at a second axial end of the sensor. The electronics module includes a resonant circuit and a power supply. The electronics module is in signal communication with the inner plate and at least one of the first cable fixture and the second cable fixture. The inner plate, the first outer plate, the second outer plate, the first cable fixture, and the second cable fixture are coupled together to form a unitary structure. The inner plate is electrically insulated from the first outer plate, the second outer plate, the first cable fixture, and the second cable fixture. The first outer plate and the second outer plate are electrically insulated from one another. The inner plate is capacitively coupled to the first outer plate and the second outer plate. The axially extending cable has an interior cavity. The at least one sensor is disposed in-line within the cable with the first cable fixture attached to a first portion of the cable and the second cable fixture attached to a second portion of the cable.

In any of the aspects or embodiments described above and herein, the at least one sensor may include a first seal in communication with the first cable fixture, the first seal configured to provide a fluid seal to prevent fluid entry into the interior cavity of the sensor, and a second seal in communication with the second cable fixture, the second seal configured to provide a fluid seal to prevent fluid entry into the interior cavity of the sensor.

In any of the aspects or embodiments described above and herein, the at least one sensor may be a plurality of sensors disposed in-line within the cable in an array. A communications lead may be attached to the electronics module of each of the plurality of sensors. The communications lead from each respective sensor may extend from that sensor through the cable to a well head end of the cable disposed outside of the well bore.

In any of the aspects or embodiments described above and herein, the system may include a cable spool disposed outside the well bore. The cable is disposed on the spool, and the spool is configured to deploy the cable into the well bore and to retrieve the cable from the well bore.

In any of the aspects or embodiments described above and herein, the system may include a system controller in communication with the at least one sensor. The at least one sensor may be operable to produce signals indicative of a type of fluid within a well fluid based on a capacitance of the well fluid when in contact with the first outer plate or the second outer plate of the sensor, or both. The system controller may be configured to determine the type of fluid within the well fluid using the signals from the sensor.

In any of the aspects or embodiments described above and herein, the system may include a system controller in communication with the at least one sensor. The at least one sensor may be operable to produce signals indicative of a presence of water within the well fluid based on an electrical resistance of the well fluid when in contact with the first outer plate or the second outer plate of the sensor, or both. The system controller may be configured to determine the presence of water within the well fluid based using the signals from the sensor.

In any of the aspects or embodiments described above and herein, the cable may have an outer diameter and the sensor may have a maximum outer diameter and the sensor maximum outer diameter is not greater than the cable outer diameter.

According to another aspect of the present disclosure, a method of sensing well fluid within a well bore is provided. The method includes a) disposing a cable having at least one in-line sensor a depth into a well bore such that the at least one sensor is disposed within a well fluid, the at least one sensor includes an inner plate, a plurality of outer plates, a first cable fixture, a second cable fixture, and an electronics module, wherein the inner plate defines an axially extending interior cavity of the sensor, the plurality of outer plates, includes a first outer plate and a second outer plate, both disposed radially outside of the inner plate, and the electronics module includes a resonant circuit and a power supply, and the electronics module is in signal communication with the inner plate and at least one of the first cable fixture and the second cable fixture, wherein the inner plate, the first outer plate, the second outer plate, the first cable fixture, and the second cable fixture are coupled together to form a unitary structure, and wherein the inner plate is electrically insulated from the first outer plate, the second outer plate, the first cable fixture, and the second cable fixture, and the first outer plate and the second outer plate are electrically insulated from one another, and the inner plate is capacitively coupled to the first outer plate and the second outer plate, and wherein the cable includes an axially extending interior cavity, and the first cable fixture of the sensor is attached to a first portion of the cable and the second cable fixture of the sensor is attached to a second portion of the cable, and the cable and at least one in-line sensor are sealed to prevent fluid entry into the interior cavity of the sensor and the interior cavity of the cable; b) operating the at least one sensor to produce signals indicative of a type of fluid within the well fluid based on a capacitance of the well fluid when in contact with the first outer plate or the second outer plate of the sensor, or both; and c) using a system controller to determine the type of fluid within the well fluid using the signals from the sensor.

In any of the aspects or embodiments described above and herein, the method may further include operating the sensor to produce signals indicative of a presence of water within the well fluid based on an electrical resistance of the well fluid when in contact with the first outer plate or the second outer plate of the sensor, or both; and may include using the system controller to determine the presence of water within the well fluid based using the signals from the sensor.

The foregoing has outlined several aspects of the present invention in order that the detailed description of the invention that follows may be better understood. Additional features and advantages of the invention will be described hereinafter which form the subject of the claims of the invention.

DETAILED DESCRIPTION

According to aspects of the present disclosure a fluid sensor 22 configured to identify fluid types within a well bore and a system 20 that utilizes one or more of such sensors 22 are provided. The sensor 22 may be used to identify the type of fluid (including types of fluid constituents within a multiphase well fluid) based on one or more electrical characteristics of the fluid in contact with a portion of the sensor 22. The present disclosure may be utilized with a variety of different structures capable of deploying a sensor 22 within a well bore and therefore is not limited to any particular structure (e.g., cable, tube, or the like). Embodiments of a sensor 22 may be configured to be a part of, or attached to, a cable (or other type structure) that is disposable within a well bore 24. To facilitate the description herein, the aforesaid structure will be referred to hereinafter generically as a "cable 26". The cable 26 and sensor 22 may be disposed within the well casing 30, or within production tubing 28 disposed within the well casing 30, or beyond the production tubing 28, or beyond the well casing 30, etc. As will be described below in greater detail, embodiments of the sensor 22 may be configured as part of a cable 26 that is spooled at the well head.

Embodiments of the sensor 22 include an inner plate 48, at least two outer plates 52, 54, an electrical insulator 50 disposed between the inner plate 48 and the outer plates 52, 54, and an electronics module 23. As will be described below, the sensor 22 is configured to produce information based on the capacitance or electrical resistance of a well fluid, or both. The at least two outer plates 52, 54 form at least a portion of the exterior of the sensor 22, and therefore are intended to be in contact with the well fluid. The inner plate 48 defines an axially extending interior cavity 60 within the sensor 22. As will be described below, the inner plate 48 is configured to receive a drive signal from the electronics module 23 and capacitively coupled to the outer plates 52, 54 which are in contact with the fluid. The interior cavity 60 is sealed to prevent well fluid from entering the cavity 60. Hence, during operation the inner plate 48 of the sensor 22 is not in contact with the well fluid. As a result, even if the outer plates 52, 54 are in contact with well fluid containing saltwater, the ability of the sensor 22 to sense capacitance will not completely short out.

Figure 1:
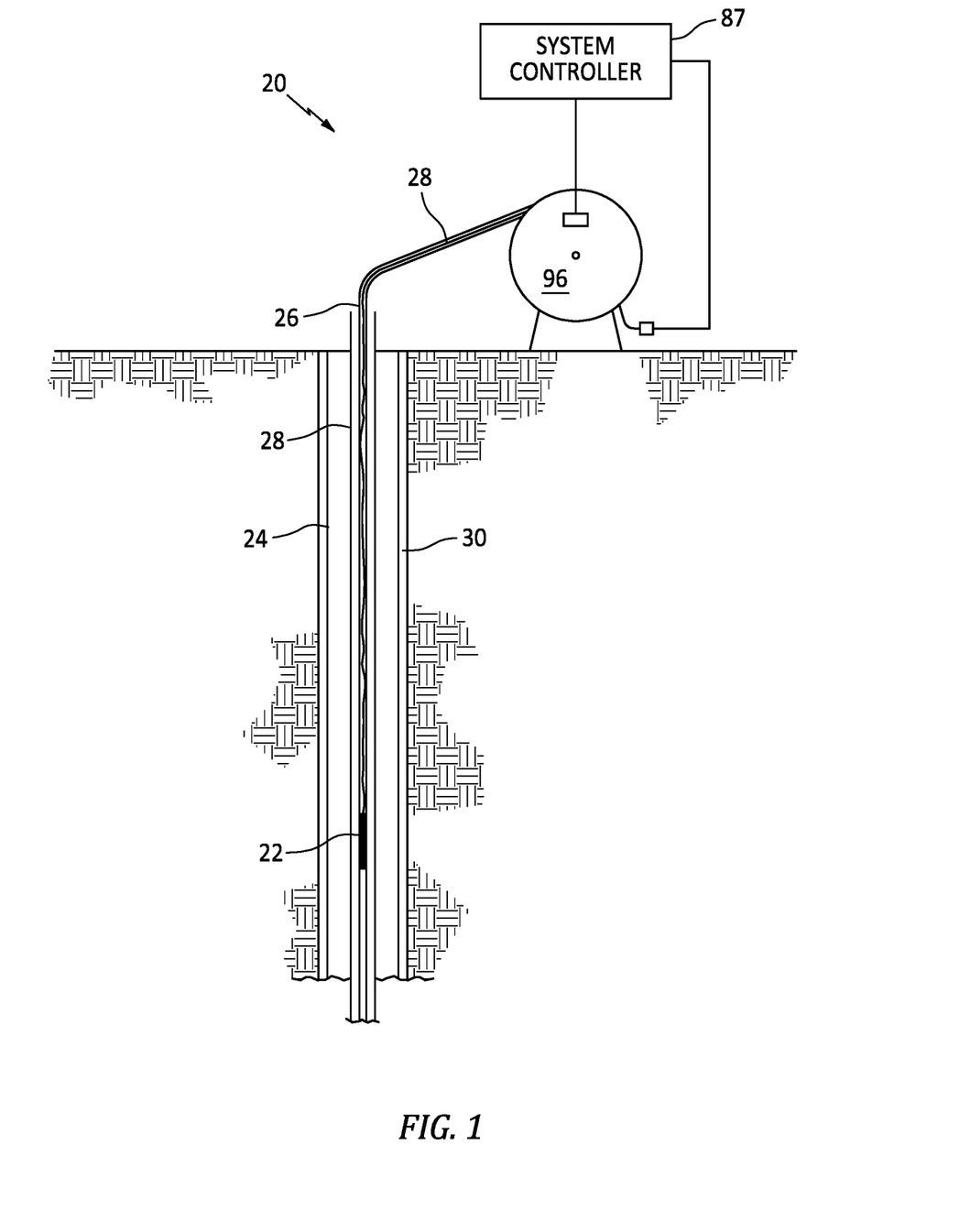
FIG. 1 is a diagrammatic view of a well bore fluid sensor system installed in a well bore.
Figure 2:
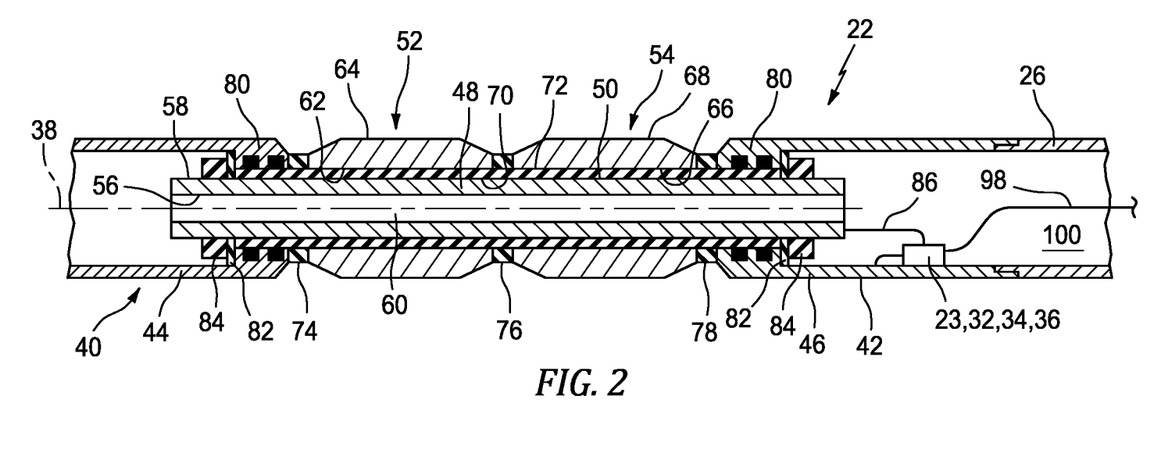
FIG. 2 is a diagrammatic cross-sectional view of a two plate sensor embodiment.

Referring to FIG. 2, a non-limiting example of a sensor 22 embodiment is shown in a cylindrical configuration that extends along a central axis 38 between a first axial end 40 and a second axial end 42. The present disclosure sensor 22 is not limited to a cylindrical configuration, however. A first cable fixture 44 is disposed at the first axial end 40 and a second cable fixture 46 is disposed at the second axial end 42. The first and second cable fixtures 44, 46 are configured for attachment to a cable 26 (e.g., see FIG. 1). The present disclosure sensor 22 can be coupled to a variety of different cable types and is not therefore limited to use with any particular cable type. In addition, the first and second cable fixtures 44, 46 may be attached to the cable 26 in a variety of different ways and the present disclosure is not limited to any particular cable attachment means. A weldment is a non-limiting example of an acceptable method of attaching the cable fixtures 44, 46 to the cable 26. In some embodiments, one or both of the first and second cable fixtures 44, 46 may be indirectly attached to the cable 26; e.g., via an intermediary structure disposed there between.

The sensor 22 embodiment shown in FIG. 2 includes an inner plate 48, an electrical insulator 50, a first outer plate 52, and a second outer plate 54. The inner plate 48 has an inner diameter surface 56 and an outer diameter surface 58. The inner diameter surface 56 of the inner plate 48 defines an interior cavity 60 of the sensor 22. The first outer plate 52 includes an inner diameter surface 62 and at least one outer diameter surface 64. The second outer plate 54 includes an inner diameter surface 66 and at least one outer diameter surface 68. The inner plate 48 and the outer plates 52, 54 are electrically conductive. The inner plate 48 and the outer plates 52, 54 may comprise the same material or different materials. A non-limiting example of an acceptable material for the inner plate 48, or the outer plates 52, 54, or both is Inconel®. The term "electrically conductive" as used herein means that the electrically conductive material (or materials) is sufficiently electrically conductive to permit the inner plate 48 and the outer plates 52, 54 to function in the manner described herein within the sensor 22. Preferably, the outer plates 52, 54 are configured to be non-reactive with well fluids; e.g., corrosion resistant, etc. The insulator 50 is disposed radially between the outer diameter surface 64 of the inner plate 48 and the inner diameter surfaces 62, 66 of the first and second outer plates 52, 54. The insulator 50 is electrically insulative. Non-limiting examples of an acceptable material for the insulator 50 include a polymer such as polyether ether ketone ("PEEK"), ceramics, and the like. The term "electrically insulative" as used herein means that the electrically insulative material is sufficiently electrically non-conductive to permit the insulator 50 to function in the manner described herein with the sensor 22. FIG. 2 diagrammatically shows a sensor 22 embodiment with an insulator 50 that is independent of the inner plate 48 and the first and second outer plates 52, 54. The insulator 50 has an inner diameter surface 70 and an outer diameter surface 72. In alternative embodiments, the insulator 50 may be attached directly to the outer diameter surface 58 of the inner plate 48; e.g., as a coating, or the like. FIG. 2 diagrammatically shows a sensor 22 embodiment with an inner plate 48 that is independent of the insulator 50 and the first and second outer plates 52, 54. In alternative embodiments, the inner plate 48 may be attached directly to the inner diameter surface 70 of the insulator 50; e.g., as a coating, or the like. In the sensor 22 embodiment shown in FIG. 2, the inner diameter surface 70 of the independent insulator 50 is contiguous with the outer diameter surface 58 of the inner plate 48, and the outer diameter surface 72 of the insulator 50 is contiguous with the inner diameter surfaces 62, 66 of the first and second outer plates 52, 54. A first electrical insulator ring 74 is disposed axially between the first cable fixture 44 and the first outer plate 52. The first electrical insulator ring 74 physically separates and electrically insulates the first cable fixture 44 and the first outer plate 52. A second electrical insulator ring 76 is disposed axially between the first outer plate 52 and the second outer plate 54. The second electrical insulator ring 76 physically separates and electrically insulates the first outer plate 52 and the second outer plate 54. A third electrical insulator ring 78 is disposed axially between the second outer plate 54 and the second cable fixture 46. The third electrical insulator ring 78 physically separates and electrically insulates the second outer plate 54 and the second cable fixture 46. The insulator rings 74, 76, 78 may comprise one or more of a variety of different electrically insulative materials (e.g., PEEK, ceramics, etc.) and are not limited to any particular material. The inner plate 48 is not electrically connected to the first or second cable fixture 44, 46. The sensor 22 may be configured with sealing structure that seals the interior of the sensor 22 to prevent well fluid disposed outside of the sensor 22 from entering the interior cavity 60 of the sensor 22. For example, in the sensor 22 embodiment shown in FIG. 2, each of the cable fixtures 44, 46 includes at least one seal 80 (e.g., an O-ring) disposed to seal between the respective cable fixture 44, 46 and the insulator 50. The present disclosure is not limited to the shown sealing arrangement. By sealing the interior of the sensor 22 in a manner that prevents well fluid disposed outside of the sensor 22 from entering the interior cavity 60 of the sensor 22 (regardless of the pressure difference across the interior and exterior of the sensor), the entry of a fluid which may act as a conductor is prevented, and any electrical shorting that may be caused by the fluid is also prevented. Hence, the seal 80 may be viewed not only as a fluid barrier, but also as an electrical barrier.

The sensor 22 embodiment shown in FIG. 2 is configured such that the elements of the sensor 22 (e.g., the inner plate 48, the insulator 50, the first and second outer plate 54, first and second cable fixtures 44, 46, etc.) are collectively assembled into a unitary assembly. The sensor 22 embodiment shown in FIG. 2 includes a washer 82 and fastener 84 pair disposed at each axial end of the inner plate 48 (e.g., each axial end of the inner plate 48 is threaded to engage a fastener 84 in the form of a nut). The washer 82 may be configured to electrically insulate the fastener 84 from the respective cable fixture 44, 46; e.g., the washer 82 may be made from an electrically insulative material, or the washer 82 may have an electrically insulative coating, etc. The fastener 84 at each axial end of the inner plate 48 mechanically holds the sensor 22 elements together as a unitary assembly. The present disclosure sensor 22 is not limited to this means of coupling the sensor 22 elements into a unitary assembly, or any particular sensor 22 assembly configuration.

As will be described in greater detail below, the configuration shown in FIG. 2 provides a desirable robust structure that is well suited for applications where mechanical strength (e.g., an ability to withstand tensile and/or compressive forces) and bending requirements are substantial; e.g., as part of a spooled cable that is deployable within the well bore.

Figure 3:
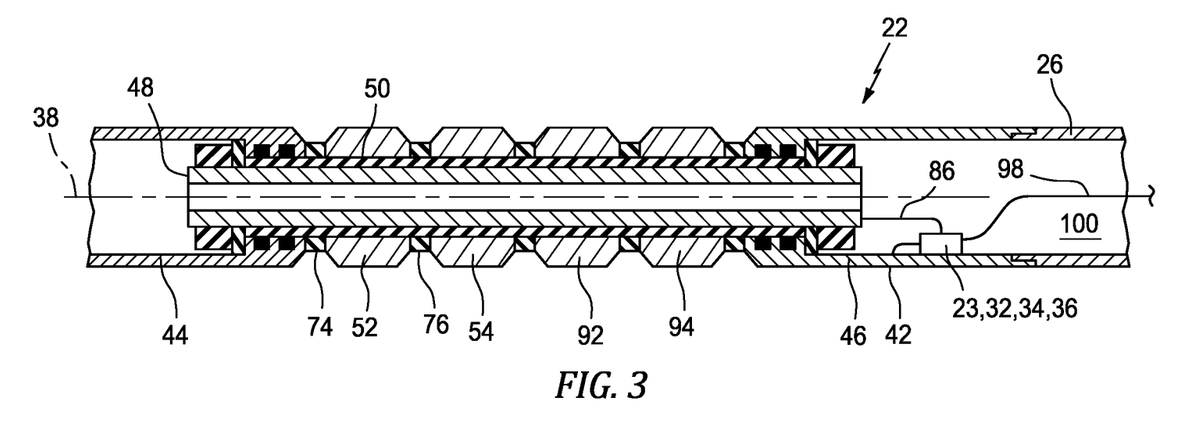
FIG. 3 is a diagrammatic cross-sectional view of a four plate sensor embodiment.

As stated above, the present disclosure sensor 22 includes at least two outer plates. To illustrate, FIG. 2 depicts a sensor 22 embodiment having two outer plates 52, 54 and FIG. 3 depicts a sensor 22 embodiment having four outer plates 52, 54, 92, 94. The sensor 22 shown in FIG. 3 is configured similarly to that described above in terms of FIG. 2; e.g., adjacent outer plates physically separated electrically insulated from one another by respective electrical insulator rings.

Embodiments of the electronics module 23 include a resonant circuit 34, a power supply 36, and a processor 32 in communication with the resonant circuit 34 and the power supply 36. In some embodiments, the processor 32 may be configured to communicate with a system controller 87 located outside of the well bore (e.g., at the well head, remote from the well head, etc.). FIG. 2 shows the electronics module 23 disposed within an interior region of a cable fixture 44, 46. The electronics module 23 may be disposed elsewhere in alternative embodiments. The resonant circuit 34 includes a resistor, an inductor, and a capacitor. The power supply may be configured to directly generate an alternating current (AC) signal. Alternatively, the AC signal may be produced by the power supply in combination with other electronic components present within the electronics module 23. Regardless of how the AC signal is produced, the electronics module 23 is configured such that the AC signal may be swept at a plurality of different frequencies within a predetermined range; e.g., between about 1 kHz and about 10 MHz. In preferred embodiments, the AC signal has a substantially sinusoidal waveform. In other embodiments, the AC signal may have a waveform other than sinusoidal; e.g., pseudo sine wave, square wave, triangular wave, etc. The processor 32 in communications with the resonant circuit 34 and the power supply 36 is configured to perform the functions described herein. The processor 32 may include any type of computing device, computational circuit, processing device, CPU, computer, or the like capable of executing a series of instructions that are stored in memory. The instructions may include an operating system, and/or executable software modules such as program files, system data, buffers, drivers, utilities, and the like. The executable instructions may apply to any functionality described herein. The processor 32 may include one or more memory devices and is not limited to any particular type of memory device. A person of skill in the art will recognize that portions of the processor 32 may assume various forms (e.g., digital signal processor, analog device, etc.) capable of performing the functions described herein. In diagrammatic view of FIG. 2, electrical leads 86 are shown connecting the electronics module 23 to the inner plate 48 and at least one of the first cable fixture 44, or the second cable fixture 46, or both. The present disclosure is not limited to any particular means of connecting the electronics module 23 to the inner plate 48 and at least one of the cable fixtures 44, 46.

FIG. 1 diagrammatically illustrates a sensor system 20 embodiment that includes at least one sensor 22 and a system controller 87. The system controller 87 is diagrammatically shown outside of the well bore; e.g., at the well head, remote from the well head, or the like. The system controller 87 is in communication with the sensor(s) 22 and may be configured to send and/or receive signals from the sensor 22, and to control aspects of the system 20 to perform the functions described herein. The system controller 87 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein. The system controller 87 may include one or more memory devices and is not limited to any particular type of memory device. The system controller 87 may include, or may be in communication with, an input device that enables a user to enter data and/or instructions, and may include, or be in communication with, an output device configured, for example to display information (e.g., a visual display or a printer), or to transfer data, etc. A person of skill in the art will recognize that portions of the system controller 87 may assume various forms (e.g., digital signal processor, analog device, etc.) capable of performing the functions described herein. Communications within the system controller 87, or to and from the system controller 87, may be accomplished by wired or wireless connections.

As indicated above, in some embodiments one or more sensors may be a part of a cable 26 that may be deployed into the well bore and retrieved from the well bore. The cable 26 is configured to withstand environmental well conditions. The present disclosure is not limited to any particular cable 26 configuration. A non-limiting example of an acceptable cable 26 is a metallic Tube Encased Cable, known as TEC wire. In some embodiments, the cable 26 may be in a form that can be collected on a spool 96; i.e., deployed into the well bore off of the spool 96 for operation and retrieved from the well bore and back onto the spool 96. The spool 96 may be in communication with the system controller 87 to control operation of the spool 96/deployment of the cable 26 and sensors 22. In this manner, the sensor(s) 22 may be deployed to a variety of different depths within the well bore during sensing operations. The cable 26 is configured as a metal clad cable that permits communication leads 98 (e.g., wires, bus connections, fiber optic lines, etc.) to extend through an internal cavity 100 that extends axially within the cable 26; e.g., a tubing encased cable or TEC wire having communication leads 98 disposed within an axial cavity 100. In those embodiments where an array of sensors 22 is included as part of a cable 26, the configuration of the present sensors 22 permits communications leads 98 from other sensors 22 to pass through the interior cavity 60 of each respective in-line sensor 22. The aforesaid communication leads 98 may extend from a respective sensor 22 to the well head via the cable 26; e.g., accessible from a well head end of the cable 26. At the well head, the communication leads 98 may be in communication with other system components such as the system controller 87. As indicated above, each cable 26 portion may be connected directly or indirectly to each sensor cable fixture 44, 46. The present disclosure is not limited to any particular manner of connecting the cable 26 to the cable fixtures 44, 46. The sensor 22 or sensors may be disposed in-line with the cable 26 and have the same general geometric profile as the cable 26 (e.g., the sensor has a maximum outer diameter that is equal to or less than the outer diameter of the cable 26) to facilitate the deployment and retrieval of the cable 26 with sensor(s) 22 in the well bore. An "in-line" configuration like this is understood to provide a significant advantage in the limited space confines of a well bore. Indeed, this aspect of the present disclosure permits the use of a small diameter cable 26 (e.g., 0.625 inch) with no protruding sensor(s) 22. In addition, as described above the unitary configuration of each sensor 22 provides a desirable robust structure that is well suited for use as a spoolable cable 26. The sensor 22 possesses desirable mechanical strength (e.g., an ability to withstand tensile and/or compressive forces and bending requirements) that facilitate a spooled application. Embodiments of the present disclosure that include an array of sensors 22 within a cable 26 configuration as described above (e.g., a spoolable cable) provide particular utility in sensing well fluid at a variety of different well depths at or about the same time.

Figure 4:
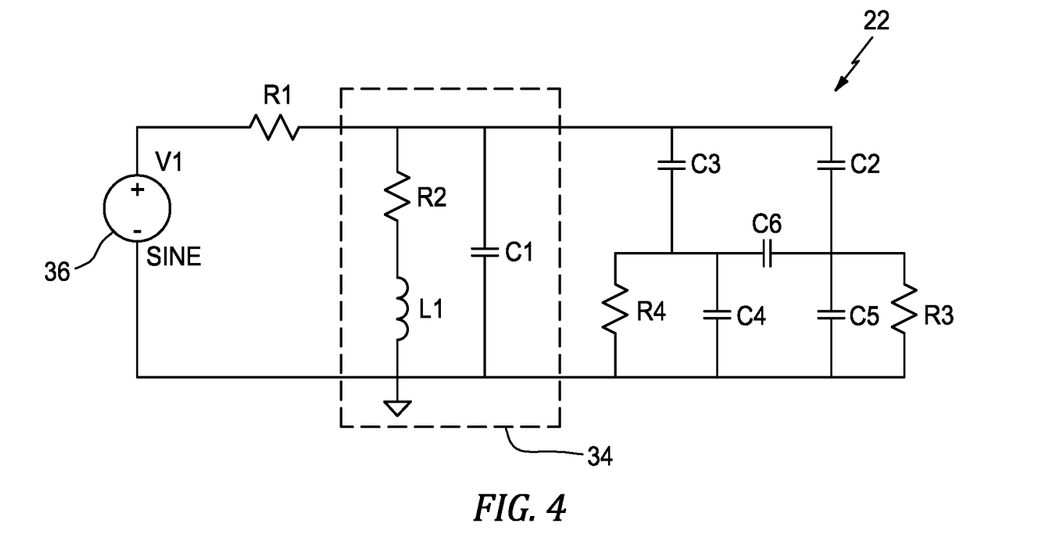
FIG. 4 is a circuit diagram illustrating aspects of the present disclosure.

FIG. 4 is a circuit diagram illustrating aspects of the present disclosure. The circuit diagram illustrates a power supply 36 (V1) that generates an AC signal. The power supply 36 may be controlled to produce the AC signal at a plurality of different frequencies; e.g., using the processor 32 to control the power supply 36. The power supply 36 is in communication with a resonant circuit 34 and an embodiment of the present disclosure sensor 22 having two outer plates. A current limiting resistor R1 may be disposed between the power supply V1 and the resonant circuit 34 and the sensor 22. The resonant circuit 34 includes a resistor R2, an inductor L1, and a capacitor C1. The two outer plate sensor 22 is shown diagrammatically as capacitors C2 and C3, indicating the capacitance between the inner plate 48 and a first outer plate 52 (that capacitance referred to as "C3") and the capacitance between the inner plate 48 and a second outer plate 54 (that capacitance referred to as "C2"). The well fluid in contact with the first and second outer plates 52, 54 represents a resistance and a capacitance within the circuit diagram; e.g., resistance R4 and capacitance C4 represent the well fluid in contact with the first outer plate 52, and resistance R3 and capacitance C5 represent the well fluid in contact with the second outer plate 54. The well fluid is then bridged between the two isolated active plates 52 and 54 and ground, as shown in FIG. 4, which will be the sensor and cable outer surface and the inner surface of the well casing or tubing. The coupling between the first and second outer plates 52, 54 is represented by C6. The resonant response of the resonant circuit 34 is independent of the resistive loading associated with the well fluid in contact with the exterior of the sensor 22.

As can be seen from this diagrammatic circuit several measurement paths are present; e.g., measurement paths between discrete sensor 22 and system 20 components and components representative of well fluid in contact with the outer plates 52, 54. A change in the dielectric properties of the well fluid will alter the value of capacitors C4, C5, and C6. Only variations in the value of C4 and C5 (i.e., the capacitance associated with the well fluid) will alter the resonant frequency of the resonant circuit 34. The resonant frequency is, therefore, a measure of the capacitance of C4 and C5 and is independent of the resistive loading associated with the well fluid; e.g., R3 and R4.

The basic relationship of a simple parallel plate capacitor can be expressed as follows:

$$C = \varepsilon A/d \qquad \text{Equation 1}$$

For purposes of describing the present sensor 22, the variables within Equation 1 may be described as: "C" is the capacitance of the sensor 22, "A" is the area of the plates, "d" is the distance between the inner plate 48 and the outer plates 52, 54, and "$\varepsilon$" is the dielectric constant of the well fluid in contact with the outer plates. In the present disclosure sensor 22 design, the configuration of the inner plate 48 and outer plates 52, 54 and areas of the plates do not change. Hence, "A" and "d" are constants and "$\varepsilon$" is the only possible variable on the right side of Equation 1. Hence, the capacitance of C4 and C5 is directly proportional to the dielectric constant of the well fluid in contact with the outer plates 52, 54, and any grounded metallic surfaces. Since the sensor 22 does not have a conventional parallel plate capacitor configuration, Equation 1 may in some instances be modified to reflect sensor 22 geometry. However, the relationship of the distance between the plates and the area is still valid. In some embodiments, calibration constants may be empirically determined to reflect the sensor 22 geometry. In addition, appropriate "C" values can be determined empirically for given applications; e.g., stored instructions may include a table of appropriate values for different applications. Dielectric constant values may vary as a function of temperature or pressure or both. Here again a calibration constant may be empirically determined for given applications.

Even a relatively small volumetric portion of water (e.g., saltwater) within the well fluid will decrease the resistivity (or increase the conductivity) of the well fluid, and therefore decrease the value of R4 and R3 accordingly. As a result, the signal amplitude of the measured output of the resonant circuit 34 will decrease. Conversely, the higher resistance associated with water-free well fluid will reduce the load on the resonant circuit 34 and increase the signal amplitude at the measured output of the resonant circuit 34. In this way there are two independent signal effects associated with the well fluid (capacitance and resistivity) that may be used by the present disclosure sensor 22 to identify constituent fluids present within the well fluid: water alters signal amplitude whereas gas, oil, and/or water will all affect the dielectric properties of the well fluid.

It is noteworthy that dielectric constant values can be very difficult if not impossible to determine using a conventional-type plate capacitor designed to have all of its plates in contact with a fluid during operation. The electrically conductive nature of water (especially saltwater) creates an electrically conductive path between the plates even if the water is only a small fraction of the total fluid present. The present disclosure sensor 22 overcomes this issue because only one of the plates (i.e., 52, 54) is in contact with the well fluid, thereby avoiding the direct electrically conductive path between the inner and outer plates. Yet, the inner plate 48 of the sensor 22 is capacitively coupled to multiple outer plates 52, 54. In fact, embodiments of the present disclosure sensor 22 can provide useful information regardless of whether water is present with well fluid.

Figure 5:
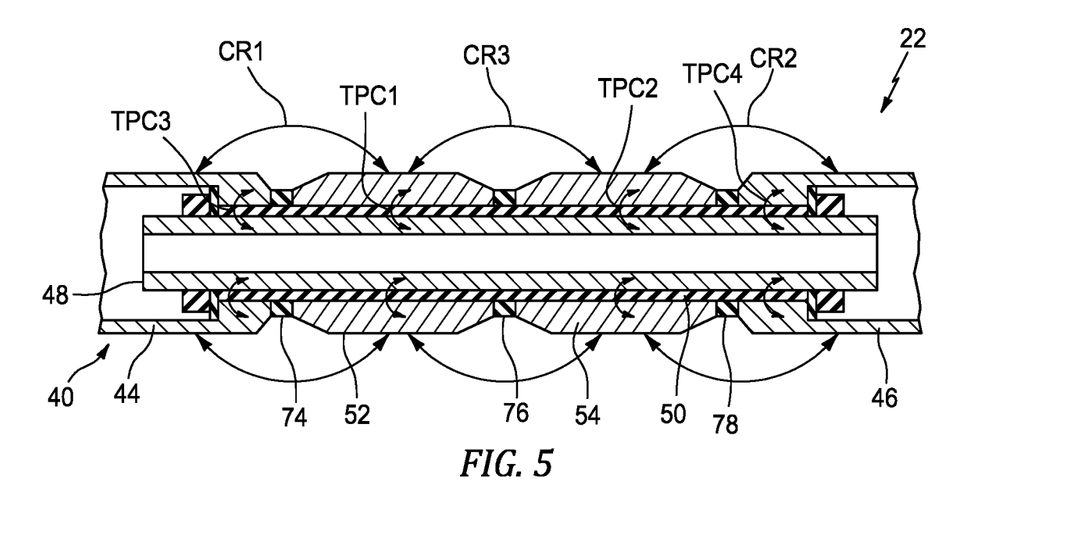
FIG. 5 is a diagrammatic cross-sectional view of a two plate sensor embodiment illustrating capacitance and resistance paths.

FIG. 5 diagrammatically illustrates sensor 22 disposed within well fluid. Capacitance between the inner plate 48 and the first outer plate 52 is diagrammatically shown as "TPC1". Capacitance between the inner plate 48 and the second outer plate 54 is diagrammatically shown as "TPC2". Stray capacitance between the inner plate 48 and the first cable fixture 44 is diagrammatically shown as "TPC3". Stray capacitance between the inner plate 48 and the second cable fixture 46 is diagrammatically shown as "TPC4". Capacitance and resistance between the first outer plate 52 and the first cable fixture 44 (or ground) is diagrammatically shown as "CR1". Capacitance and resistance between the second outer plate 54 and the second cable fixture 46 (or ground) is diagrammatically shown as "CR2". Capacitance and resistance between the first and second outer plates 52, 54 is diagrammatically shown as "CR3".

Figure 6:
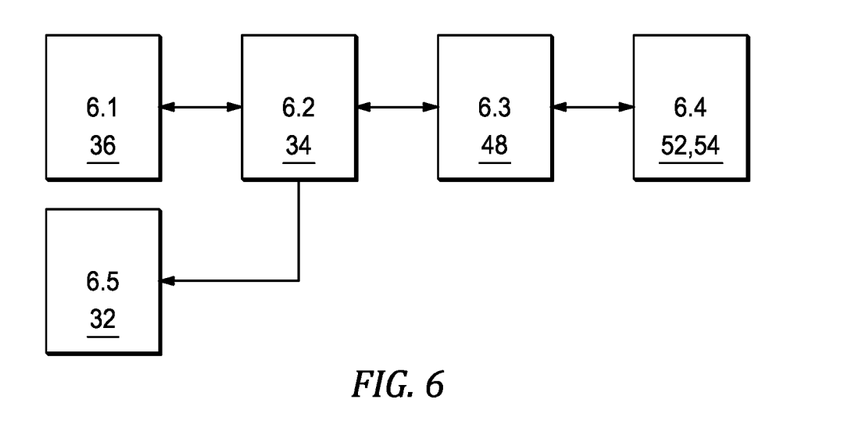
FIG. 6 is a block diagram illustrating an operation mode of the present disclosure sensor and system.

An example of how the present disclosure may be operated is shown in the block diagram of FIG. 6. Block 6.1 represents a power supply 36 operable to produce a static or swept AC signal that feeds power into the resonant circuit 34 represented by block 6.2. The resonant circuit 34 in turn feeds power into the inner plate 48 (represented by block 6.3) of the sensor 22. The inner plate 6.3 is capacitively coupled to the outer plates and fluid represented by block 6.4. The signal amplitude in the resonant circuit 34 determined as a function of the swept frequencies by the sensor processor 32 is represented by block 6.5. The signal amplitude output of the resonant circuit 34 as a function of frequency can be communicated to the system controller 87 for a determination of the fluid type(s) present within the well fluid; e.g., based on empirical data.

Figure 7:
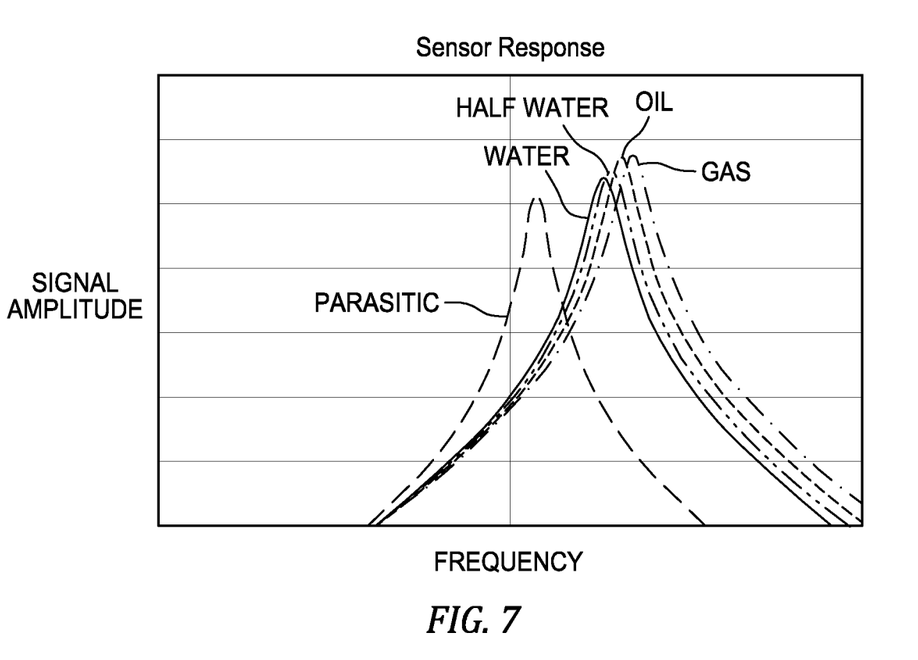
FIG. 7 is a graph of capacitance versus frequency illustrating capacitance and signal amplitude associated with different well fluid constituents.

FIG. 7 graphically illustrates an example of output that may be obtained by the resonant circuit 34; e.g., signal amplitude as a function of frequency. FIG. 7 specifically illustrates a graph of signal amplitude versus frequency for different fluid constituents including a parasitic signal. The "half-water" curve reflects a sensor that is half immersed in water. The capacitance of the complete system (influenced by the well fluid in contact with the outer plates 52, 54) alters the resonant frequency within the resonant circuit 34. The amount of water present within the well fluid, if any, alters the amplitude of the signal measured within the resonant circuit 34 generally and specifically at the resonant frequency. More specifically, water (e.g., particularly saltwater) within the well fluid decreases the resistivity of the well fluid and causes a decrease in the amplitude of the signal within the resonant circuit 34. It can be seen, therefore, that if a present disclosure sensor 22 is immersed in well fluid containing water, oil, or gas, the dielectric properties of the well fluid constituents will influence the sensor 22 capacitance as indicated by the resonant circuit 34 signals. It can also be seen that well fluid containing some amount of water (e.g., particularly saltwater) will influence the signal amplitude measured at the resonant circuit 34. These resonant circuit 34 signal properties can be used to determine characteristics of the well fluid in contact with the sensor 22.

Figure 8A:
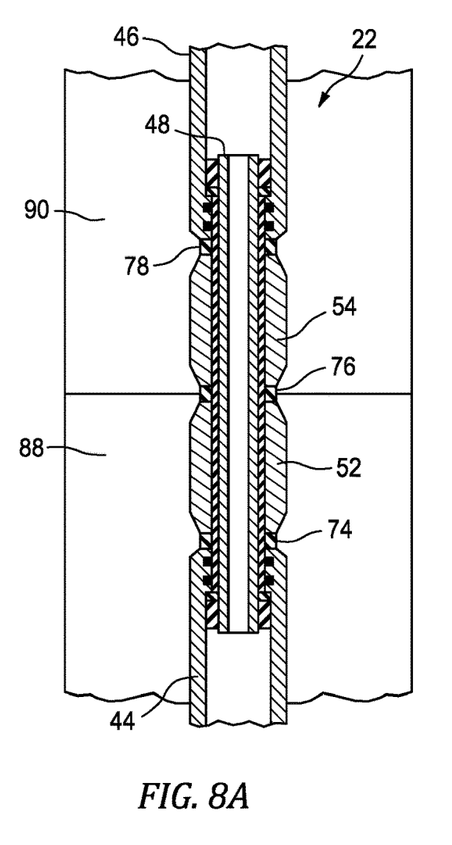
FIG. 8A is a diagrammatic cross-sectional view of a two plate sensor embodiment in contact with a first well fluid body and a second well fluid body.
Figure 8B:
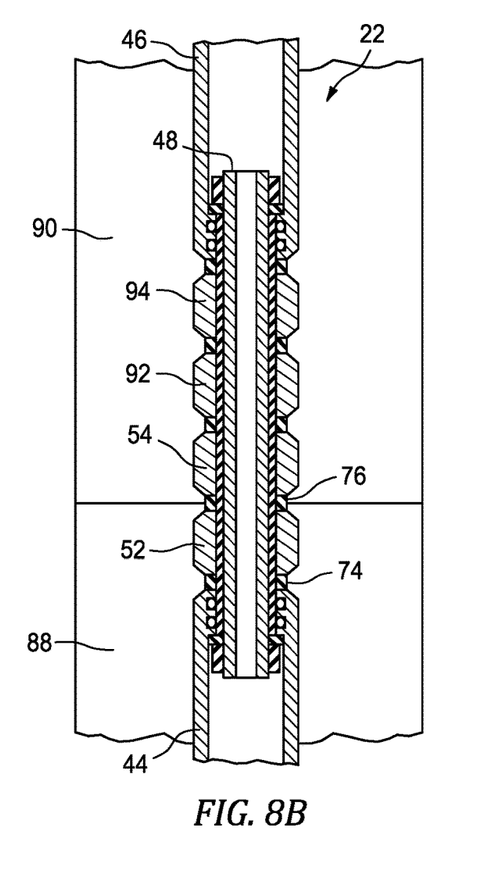
FIG. 8B is a diagrammatic cross-sectional view of a four plate sensor embodiment in contact with a first well fluid body and a second well fluid body.

FIGS. 8A and 8B show a fluid sensing scenario where the sensor 22 is disposed at a boundary between two different well fluid bodies. FIG. 8A shows a two outer plate sensor 22 embodiment where the boundary between two different well fluid bodies 88, 90 is disposed at the insulator ring 76 separating the first outer plate 52 and the second outer plate 54. In FIG. 8A, a first well fluid body 88 containing some amount of saltwater is in contact with the first outer plate 52 and a second well fluid body 90 without any saltwater is in contact with the second outer plate 54. In regard to capacitance and resistance associated with the first outer plate 52, the first well fluid body 88 is relevant (because only it is in contact with the first outer plate 52) and the second well fluid body 90 is substantially irrelevant (because it is not in contact with the first outer plate 52). Similarly, in regard to capacitance and resistance associated with the second outer plate 54, the second well fluid body 90 is relevant (because only it is in contact with the second outer plate 54) and the first well fluid body 88 is substantially irrelevant (because it is not in contact with the second outer plate 54). Despite the fact that there is a common inner plate 48 and the effects of these two fluid bodies 88, 90 are combined in the sensor 22 output, the sensor 22 will nevertheless cause the resonant circuit 34 to produce a different signal than if there was only one single solid outer plate in contact with two distinct well fluid bodies; e.g., well fluid bodies 88, 90. In such a single outer plate scenario, the saltwater present within a first well fluid body may short out the capacitance effect and inhibit the ability of a sensor to produce useful information regarding the fluids present within the well fluids. Practically speaking, well fluid portions 88, 90 having different characteristics are almost never as well defined as is suggested in FIG. 8A, and in fact most of the time well fluid in contact with the sensor 22 is moving relative to the sensor 22; e.g., flowing past the sensor 22. However, very often well fluids are turbulent or travel axially in a non-uniform manner (e.g., "slugging"). The present disclosure sensor 22 embodiments having two or more outer plates 52, 54 each capable of independently providing capacitance and resistance information will cause the sensor 22 to respond differently than they would in the presence of well mixed fluids. This information can be useful to the operator.

FIG. 8B shows a four outer plate sensor 22 embodiment where the boundary between two different well fluid bodies 88, 90 is disposed at the insulator ring 76 separating the first outer plate 52 and the second outer plate 54. In FIG. 8B, a first well fluid body 88 containing some amount of saltwater is in contact with the first outer plate 52 and a second well fluid body 90 without any saltwater is in contact with the second, third, and fourth outer plates 54, 92, 94. Here again, sensor 22 embodiments having a plurality of outer plates each capable of independently providing capacitance and resistance information will cause the sensor 22 to respond differently than they would in the presence of well mixed fluids. It is believed that a sensor 22 having multiple independent outer plates can provide even more useful information to an operator relating to well fluid characteristics; e.g., by reducing the impact of saltwater shorting outer plates.

While the principles of the disclosure have been described above in connection with specific apparatuses and methods, it is to be clearly understood that this description is made only by way of example and not as limitation on the scope of the disclosure. Specific details are given in the above description to provide a thorough understanding of the embodiments. However, it is understood that the embodiments may be practiced without these specific details.

It is noted that the embodiments may be described as a process which is depicted as a flowchart, a flow diagram, a block diagram, etc. Although any one of these structures may describe the operations as a sequential process, many of the operations can be performed in parallel or concurrently. In addition, the order of the operations may be rearranged. A process may correspond to a method, a function, a procedure, a subroutine, a subprogram, etc.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements unless the context clearly indicates otherwise. As used herein, "comprises" means "includes." Thus, "comprising A or B," means "including A or B, or A and B," without excluding additional elements.

It is noted that various connections are set forth between elements in the present description and drawings (the contents of which are included in this disclosure by way of reference). It is noted that these connections are general and, unless specified otherwise, may be direct or indirect and that this specification is not intended to be limiting in this respect. Any reference to attached, fixed, connected or the like may include permanent, removable, temporary, partial, full and/or any other possible attachment option.

No element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprise", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein. For example, in the exemplary embodiments described above within the Detailed Description portion of the present specification, elements may be described as individual units and shown as independent of one another to facilitate the description. In alternative embodiments, such elements may be configured as combined elements.

The invention claimed is:

1. A well bore fluid sensor, comprising:
   an inner plate defining an axially extending interior cavity of the sensor;
   a plurality of outer plates, including a first outer plate and a second outer plate, disposed radially outside of the inner plate;
   a first cable fixture disposed at a first axial end of the sensor and a second cable fixture disposed at a second axial end of the sensor; and
   an electronics module that includes a resonant circuit and a power supply, the electronics module in signal communication with the inner plate and at least one of the first cable fixture and the second cable fixture;
   wherein the inner plate, the first outer plate, the second outer plate, the first cable fixture, and the second cable fixture are coupled together to form a unitary structure; and
   wherein the inner plate is electrically insulated from the first outer plate, the second outer plate, the first cable fixture, and the second cable fixture, and the first outer plate and the second outer plate are electrically insulated from one another, and the inner plate is capacitively coupled to the first outer plate and the second outer plate.

2. The sensor of claim 1, wherein the sensor is cylindrically configured, the inner plate having an inner diameter surface and an outer diameter surface, the inner diameter surface defining the interior cavity.

3. The sensor of claim 1, wherein the first cable fixture is configured for attachment to a first cable portion, and the second cable fixture is configured for attachment to a second cable portion in a manner that the sensor is disposed in-line between the first cable portion and the second cable portion.

4. The sensor of claim 3, wherein the sensor further comprises a first seal in communication with the first cable fixture, the first seal configured to provide a fluid seal to prevent fluid entry into the interior cavity of the sensor, and a second seal in communication with the second cable fixture, the second seal configured to provide a fluid seal to prevent fluid entry into the interior cavity of the sensor.

5. The sensor of claim 1, further comprising an electrical insulator disposed between the inner plate and the first outer plate and the second outer plate.

6. The sensor of claim 5, wherein the sensor is cylindrically configured, the inner plate having an inner diameter surface and an outer diameter surface, the inner diameter surface defining the interior cavity, and the electrical insulator is attached to a first portion of inner plate outer diameter surface disposed radially between the inner plate and the first outer plate, and attached to a second portion of inner plate outer diameter surface disposed radially between the inner plate and the second outer plate.

7. The sensor of claim 1, further comprising:
an electrical insulator disposed between the inner plate and the first outer plate and the second outer plate, wherein the electrical insulator includes an inner diameter surface and an outer diameter surface, and the inner plate is attached to an inner diameter surface of the electrical insulator;
a first electrical insulator ring disposed between the first cable fixture and the first outer plate;
a second electrical insulator ring disposed between the second outer plate and the second cable fixture; and
a third electrical insulator ring disposed between the first outer plate and the second outer plate.

8. The sensor of claim 1, wherein the electronics module further includes a processor in communication with the resonant circuit and the power supply, the processor configured to receive signals from the resonant circuit and to control the power supply.

9. The sensor of claim 1, wherein the sensor is operable to sense a type of fluid within a well fluid based on a capacitance of the well fluid when in contact with the first outer plate or the second outer plate of the sensor, or both.

10. The sensor of claim 1, wherein the sensor is operable to sense a type of fluid within a well fluid based on a capacitance of the well fluid when in contact with said plurality of outer plates.

11. The sensor of claim 1, wherein the sensor is operable to determine a presence of water within a well fluid based on an electrical resistance of the well fluid when in contact with the first outer plate or the second outer plate of the sensor, or both.

12. A well bore fluid sensor system operable to sense well fluid within a well bore, the system comprising:
at least one sensor having:
an inner plate defining an axially extending interior cavity of the sensor;
a plurality of outer plates, including a first outer plate and a second outer plate, disposed radially outside of the inner plate;
a first cable fixture disposed at a first axial end of the sensor and a second cable fixture disposed at a second axial end of the sensor; and
an electronics module that includes a resonant circuit and a power supply, the electronics module in signal communication with the inner plate and at least one of the first cable fixture and the second cable fixture;
wherein the inner plate, the first outer plate, the second outer plate, the first cable fixture, and the second cable fixture are coupled together to form a unitary structure; and
wherein the inner plate is electrically insulated from the first outer plate, the second outer plate, the first cable fixture, and the second cable fixture, and the first outer plate and the second outer plate are electrically insulated from one another, and the inner plate is capacitively coupled to the first outer plate and the second outer plate; and
an axially extending cable having an interior cavity, wherein the at least one sensor is disposed in-line within the cable with the first cable fixture attached to a first portion of the cable and the second cable fixture attached to a second portion of the cable.

13. The sensor system of claim 12, wherein the at least one sensor further comprises a first seal in communication with the first cable fixture, the first seal configured to provide a fluid seal to prevent fluid entry into the interior cavity of the sensor, and a second seal in communication with the second cable fixture, the second seal configured to provide a fluid seal to prevent fluid entry into the interior cavity of the sensor.

14. The sensor system of claim 13, wherein the at least one sensor is a plurality of sensors disposed in-line within the cable in an array; and
a communications lead is attached to the electronics module of each of the plurality of sensors, and the communications lead from each respective sensor extends from that sensor through the cable to a well head end of the cable disposed outside of the well bore.

15. The sensor system of claim 14, wherein the system includes a cable spool disposed outside the well bore, the cable disposed on the spool, and the spool configured to deploy said cable into the well bore and to retrieve said cable from the well bore.

16. The sensor system of claim 12, wherein the system includes a system controller in communication with the at least one sensor; and
wherein the sensor is operable to produce signals indicative of a type of fluid within a well fluid based on a capacitance of the well fluid when in contact with the first outer plate or the second outer plate of the sensor, or both; and
wherein the system controller is configured to determine said type of fluid within the well fluid using the signals from the sensor.

17. The sensor system of claim 12, wherein the system includes a system controller in communication with the at least one sensor; and
wherein the sensor is operable to produce signals indicative of a presence of water within the well fluid based on an electrical resistance of the well fluid when in contact with the first outer plate or the second outer plate of the sensor, or both; and
wherein the system controller is configured to determine said presence of water within the well fluid based using the signals from the sensor.

18. The sensor of claim 12, wherein the cable has an outer diameter, and the sensor has a maximum outer diameter, and the sensor maximum outer diameter is not greater than the cable outer diameter.

19. A method of sensing well fluid within a well bore, comprising:

disposing a cable having at least one in-line sensor a depth into a well bore such that the at least one sensor is disposed within a well fluid, the at least one sensor comprising:
- an inner plate defining an axially extending interior cavity of the sensor;
- a plurality of outer plates, including a first outer plate and a second outer plate, both disposed radially outside of the inner plate;
- a first cable fixture and a second cable fixture; and
- an electronics module that includes a resonant circuit and a power supply, the electronics module in signal communication with the inner plate and at least one of the first cable fixture and the second cable fixture;
- wherein the inner plate, the first outer plate, the second outer plate, the first cable fixture, and the second cable fixture are coupled together to form a unitary structure; and
- wherein the inner plate is electrically insulated from the first outer plate, the second outer plate, the first cable fixture, and the second cable fixture, and the first outer plate and the second outer plate are electrically insulated from one another, and the inner plate is capacitively coupled to the first outer plate and the second outer plate; and wherein the cable includes an axially extending interior cavity, and the first cable fixture of the sensor is attached to a first portion of the cable and the second cable fixture of the sensor is attached to a second portion of the cable, and the cable and at least one in-line sensor are sealed to prevent fluid entry into the interior cavity of the sensor and the interior cavity of the cable;

operating the at least one sensor to produce signals indicative of a type of fluid within the well fluid based on a capacitance of the well fluid when in contact with the first outer plate or the second outer plate of the sensor, or both; and using a system controller to determine said type of fluid within the well fluid using the signals from the sensor.

20. The method of claim 19, further comprising operating the sensor to produce signals indicative of a presence of water within the well fluid based on an electrical resistance of the well fluid when in contact with the first outer plate or the second outer plate of the sensor, or both; and using the system controller to determine said presence of water within the well fluid based using the signals from the sensor.

* * * * *